(12) United States Patent
Vachicouras et al.

(10) Patent No.: US 11,628,297 B2
(45) Date of Patent: Apr. 18, 2023

(54) BIOMEDICAL DEVICE COMPRISING A MECHANICALLY ADAPTIVE MEMBER

(71) Applicant: ECOLE POLYTECHNIQUE FEDERALE DE LAUSANNE (EPFL), Lausanne (CH)

(72) Inventors: Nicolas Vachicouras, Chambesy (CH); Jennifer Macron, Saint Julien en Genevois (FR); Stephanie P. Lacour, Etoy (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 0 days.

(21) Appl. No.: 16/745,265

(22) Filed: Jan. 16, 2020

(65) Prior Publication Data
US 2020/0230401 A1    Jul. 23, 2020

(30) Foreign Application Priority Data

Jan. 18, 2019    (EP) .................................... 19152581

(51) Int. Cl.
*A61N 1/05*    (2006.01)
*A61L 31/14*    (2006.01)

(52) U.S. Cl.
CPC .......... *A61N 1/0587* (2013.01); *A61L 31/145* (2013.01); *A61N 1/0507* (2013.01);
(Continued)

(58) Field of Classification Search
None
See application file for complete search history.

(56) References Cited

U.S. PATENT DOCUMENTS

| | | | | |
|---|---|---|---|---|
| 5,653,742 A | * | 8/1997 | Parker | ...................... A61D 7/00 607/116 |
| 7,146,227 B2 | * | 12/2006 | Dadd | ................... A61N 1/0541 607/57 |

(Continued)

FOREIGN PATENT DOCUMENTS

| | | |
|---|---|---|
| WO | 2004/095536 A2 | 11/2004 |
| WO | 2008/085904 A1 | 7/2008 |

(Continued)

OTHER PUBLICATIONS

Kim et al., "Dissolvable Films of Silk Fibroin for Ultrathin, Conformal Bio-integrated Electronics," *Nat Mater.* 9(6):511-517, 2010.

(Continued)

*Primary Examiner* — Carl H Layno
*Assistant Examiner* — Manolis Pahakis
(74) *Attorney, Agent, or Firm* — Seed Intellectual Property Law Group LLP

(57) ABSTRACT

A biomedical device having improved handling features to be easily inserted into a cavity or recess is disclosed, as well as methods for using thereof, said device comprising a flat and soft substrate, comprising electrically conductive tracks, configured to interface a biological surface; and a rigid member located on a portion of said flat and soft substrate, said member being substantially composed of a mechanically adaptive material being fully or partially degradable upon a degrading/softening trigger.

12 Claims, 4 Drawing Sheets

(52) U.S. Cl.
CPC ......... *A61N 1/0509* (2013.01); *A61N 1/0543* (2013.01); *A61N 1/0553* (2013.01)

(56) References Cited

U.S. PATENT DOCUMENTS

| | | | |
|---|---|---|---|
| 7,269,461 B2 * | 9/2007 | Dadd | A61N 1/0541 607/57 |
| 7,894,916 B2 * | 2/2011 | Gibson | A61N 1/0541 607/57 |
| 8,440,546 B2 * | 5/2013 | Nuzzo | H01L 21/02521 438/472 |
| 8,617,097 B2 * | 12/2013 | Dadd | A61K 9/0009 604/57 |
| 9,555,583 B1 * | 1/2017 | Dirk | B33Y 10/00 |
| 9,795,718 B1 * | 10/2017 | Cao | A61N 1/05 |
| 10,130,274 B2 * | 11/2018 | Voros | A61N 1/0551 |
| 10,240,688 B2 * | 3/2019 | Besse | F16K 99/0015 |
| 10,704,167 B2 * | 7/2020 | Sorin | G01L 1/20 |
| 10,925,543 B2 * | 2/2021 | Rogers | A61L 31/028 |
| 2004/0122501 A1 * | 6/2004 | Dadd | A61N 1/0541 607/137 |
| 2004/0172118 A1 * | 9/2004 | Gibson | A61N 1/0541 607/137 |
| 2006/0015024 A1 * | 1/2006 | Brister | A61B 5/14865 600/345 |
| 2007/0073130 A1 * | 3/2007 | Finch | A61N 1/0551 600/377 |
| 2007/0232983 A1 * | 10/2007 | Smith | A61N 1/0444 604/20 |
| 2009/0259281 A1 * | 10/2009 | Weiss | A61N 1/05 607/116 |
| 2010/0041972 A1 * | 2/2010 | Mason | A61B 5/296 600/372 |
| 2011/0230735 A1 * | 9/2011 | Wolfe | A61B 5/14503 204/403.14 |
| 2011/0306878 A1 * | 12/2011 | Desimone | A61N 1/30 600/431 |
| 2011/0307042 A1 * | 12/2011 | DeCarmine | A61N 1/05 607/116 |
| 2012/0004715 A1 * | 1/2012 | Ramachandran | A61N 1/0541 607/137 |
| 2012/0035615 A1 * | 2/2012 | Koester | A61B 17/3468 607/137 |
| 2012/0123318 A1 * | 5/2012 | Ek | A61N 1/0551 604/20 |
| 2012/0141572 A1 * | 6/2012 | Hessler | A61L 27/34 606/1 |
| 2012/0296444 A1 * | 11/2012 | Greenberg | A61N 1/0531 607/152 |
| 2013/0090542 A1 * | 4/2013 | Kipke | A61B 5/24 607/116 |
| 2013/0131482 A1 * | 5/2013 | Fedder | B29C 41/04 264/494 |
| 2013/0144145 A1 * | 6/2013 | Meng | A61B 5/24 600/377 |
| 2013/0144369 A1 * | 6/2013 | Elias | A61N 1/0551 607/116 |
| 2014/0163390 A1 | 6/2014 | Rogers et al. | |
| 2014/0206967 A1 * | 7/2014 | Laramy | A61B 5/6852 600/345 |
| 2014/0213866 A1 * | 7/2014 | Simpson | A61B 5/14503 600/345 |
| 2014/0276748 A1 * | 9/2014 | Ku | A61B 18/18 606/33 |
| 2014/0378993 A1 * | 12/2014 | Shah | A61B 5/24 428/172 |
| 2015/0018659 A1 * | 1/2015 | Ware | A61L 31/06 600/378 |
| 2015/0143925 A1 * | 5/2015 | Vandeparre | H05K 1/0373 73/862.626 |
| 2015/0151107 A1 * | 6/2015 | Schouenborg | A61M 31/002 604/20 |
| 2015/0202351 A1 * | 7/2015 | Kaplan | A61L 31/047 607/116 |
| 2015/0289788 A1 * | 10/2015 | Simpson | A61B 5/14532 225/2 |
| 2016/0058316 A1 * | 3/2016 | Vitale | A61N 1/0534 156/60 |
| 2016/0073920 A1 * | 3/2016 | Kassegne | A61B 5/24 430/319 |
| 2016/0120472 A1 * | 5/2016 | Kub | C23C 16/405 216/13 |
| 2017/0086301 A1 * | 3/2017 | Minev | H05K 3/005 |
| 2017/0251976 A1 * | 9/2017 | Schouenborg | A61L 31/10 |
| 2018/0001081 A1 * | 1/2018 | Minev | H01L 23/4985 |
| 2018/0124926 A1 * | 5/2018 | Modi | H05K 1/111 |
| 2018/0207863 A1 * | 7/2018 | Porter | B29C 64/129 |
| 2019/0060518 A1 * | 2/2019 | Schouenborg | A61B 5/686 |
| 2019/0061153 A1 * | 2/2019 | Gregg | B25J 9/1633 |
| 2019/0126043 A1 * | 5/2019 | Cullen | A61N 1/0536 |
| 2019/0217082 A1 * | 7/2019 | Modi | A61B 5/24 |
| 2019/0336771 A1 * | 11/2019 | Voit | A61N 1/36062 |
| 2020/0094466 A1 * | 3/2020 | Vachicouras | B32B 27/281 |
| 2020/0188660 A1 * | 6/2020 | Franke | A61B 5/1107 |
| 2021/0100509 A1 * | 4/2021 | Villada | A61B 5/4806 |

FOREIGN PATENT DOCUMENTS

| | | | |
|---|---|---|---|
| WO | 2015/172894 A1 | 11/2015 | |
| WO | 2016/110564 A1 | 7/2016 | |
| WO | 2016/145299 A1 | 9/2016 | |
| WO | WO-2018005365 A1 * | 1/2018 | ............ H05K 1/118 |
| WO | 2018/100005 A1 | 6/2018 | |

OTHER PUBLICATIONS

Lo et al., "Coating flexible probes with an ultra fast degrading polymer to aid in tissue insertion," *Biomed Microdevices.* 17(2):34, 2015. (22 pages).

Nguyen et al., "Mechanically-complaint intracortical implants reduce the neuroinflammatory response," *J. Neural Eng 11*:056014, 2014, (15 pages).

Rosset et al., "Flexible and Stretchable Electrodes for Dielectric Elastomer Actuators," *Applied Physics A,* 110(2):281-307, 2013.

* cited by examiner

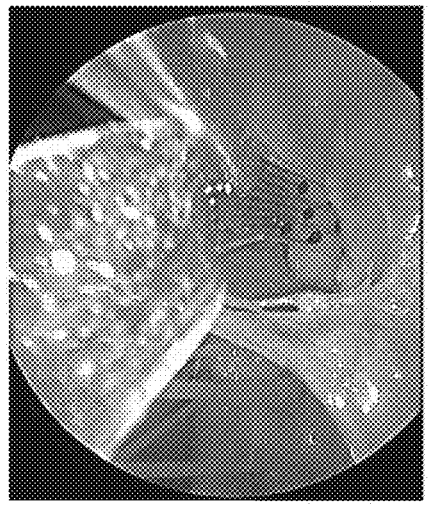
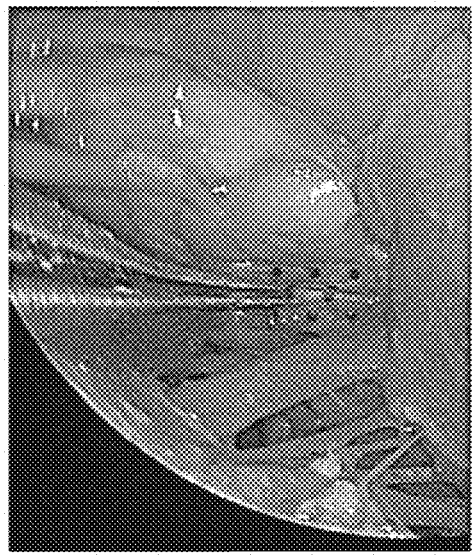
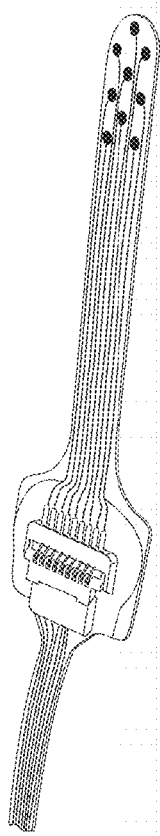
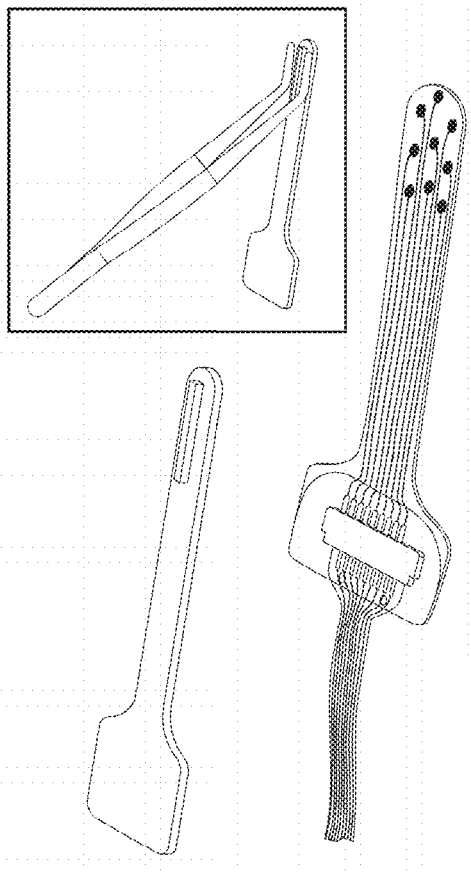
Figure 3A
Figure 3B

# BIOMEDICAL DEVICE COMPRISING A MECHANICALLY ADAPTIVE MEMBER

RELATED APPLICATION

The present application claims the benefit of EP patent application serial number 19152581.5, filed on Jan. 18, 2019.

BACKGROUND

Technical Field

The present disclosure belongs to the fields of biomedical devices.

Description of the Related Art

Current clinical electrode array implants (such as neural implants) that aim at interfacing with the surface of tissues (e.g. brain, spinal cord, heart, etc) are fabricated with relatively stiff materials providing both easy handling and surgical positioning. However, the implant rigidity has been demonstrated to be responsible for inflammatory response of the surrounding tissues after few months or years of implantation due to a mechanical mismatch. Moreover, a rigid implant won't be able to conform to the complex curvature typically present in a target biological tissue (such as the brain, spinal cord, or heart) and thus the interface won't be optimal in its interaction with said tissue, leading to poor functional capabilities (for instance, stimulation or recording of electrical stimuli), and/or generation of side effects in operation, typically during electrical stimulation.

To overcome this issue, researchers have proposed a new generation of biomedical devices and interfaces based on elastomeric substrates. Thanks to their mechanical properties (soft and flexible), these devices are well biointegrated. Even though softness is advantageous for such devices once permanently implanted in the body, it makes them delicate to handle with tweezers by surgeons and almost impossible to properly insert in the different cavities or recesses of a subject's body without carriers assistance or additional tissue traumatism. This can be highly problematic in many cases where such devices, e.g. fixed or temporary implants, need to be inserted into hardly or barely reachable spots such as the brain stem or internal organs in a minimally invasive way.

Some attempts have been done in the past to attempt to overcome the above problems and/or drawbacks. For instance, Lo, Meng-chen, et al. (Biomedical microdevices 17.2 (2015): 34) describe the coating of flexible penetrating probes with an ultra-fast degrading polymer to aid in tissue insertion. A polymer coating of SU-8 on a flexible intracortical probe rigidifies the probe (increasing the bending stiffness of the assembly) as a function of the coating thickness. After insertion the polymer coating degrades (time scale ~40 min) and the SU8 flexible probe remains inserted.

Kim, Dae-Hyeong, et al. (Nature materials 9.6 (2010): 511) describe dissolvable films of silk fibroin for ultrathin conformal bio-integrated electronics. An ultrathin electronic device is supported by bioresorbable substrates of silk able to interface with brain tissues. The technology provides a good handling of the device during fabrication and implant due to stiff silk backing and a reduced thickness of substrate (improving conformal contact between the device and the targeted tissues) after complete dissolution of silk in biological fluids. However, this kind of implant is not suitable for insertion into a cavity or recess, as the backing rigidifies the entire structure, thus rendering it brittle and fragile upon bending.

Nguyen, Jessica K., et al. (Journal of neural engineering 11.5 (2014): 056014) describe mechanically-compliant intracortical penetrating implants that reduce the neuroinflammatory response. In this case, a PVA polymer coating is placed on stiff intracortical probes to improve biocompatibility of the implants with tissues and reduce neuroinflammation. As for the above article from Lo, Meng-chen, et al., the described device is not configured for placement on a biological surface, but rather for insertion (penetration) into a tissue.

Despite all the proposed solutions, what is still lacking is a soft and flexible biomedical device such as a surface implant, compliant and conformable to biological surfaces, being at the same time easily handable by an operator upon surgical operations.

BRIEF SUMMARY

In order to address and overcome the above-mentioned drawbacks of the prior art solutions, the present inventors developed a new kind of biomedical device having improved handling features and capabilities.

A purpose of the present disclosure is therefore that of providing a biomedical device allowing to overcome or at least reduce the above summarized drawbacks affecting biomedical devices according to the prior art.

In particular, a first purpose of the present disclosure is that of providing a biomedical device having sufficient robustness to be easily handled and manipulated by a practitioner without being fragile or brittle.

A further purpose of the present disclosure is that of providing a biomedical device having improved handling features to be easily inserted into a cavity or recess, these being a bodily cavity or recess of a subject and/or a cavity or a bore of a surgical tool or the like.

Still a further of the present disclosure is that of providing a biomedical device having optimized handling properties during surgical operations without compromising its mechanical properties and/or biocompatibility with bodily tissues of a subject upon insertion and/or implant. All those aims have been accomplished with the present disclosure, as described herein and in the appended claims.

In general terms, a purpose of the present disclosure is that of enabling the insertion of soft elastomer-based devices or implants in various locations of a subject's body; as a way of example, neural interfaces can be obtained that might be advantageously implanted on brain targets such as the superior temporal sulcus of the brain, the lateral recess of the fourth ventricle to access the auditory brainstem or the surface of the spinal cord.

In view of the above summarized drawbacks and/or problems affecting biomedical devices of the prior art, according to the present disclosure there is provided a biomedical device according to claim 1.

In particular, according to an embodiment of the present disclosure there is provided an electrical or electronic biomedical device comprising:

a) a flat and soft substrate, comprising electrically conductive tracks, configured to interface a biological surface; and b) a rigid member located on a portion of said flat and soft substrate, said member being substantially composed of a mechanically adaptive material being fully or partially degradable upon a degrading, such as a softening, trigger.

According to the present disclosure there is further provided a method of manufacturing an electrical or electronic biomedical device, said biomedical device having a flat and soft substrate, said method comprising a step of placing a rigid member on a portion of said flat and soft substrate, said member being substantially composed of a mechanically adaptive material being fully or partially degradable upon a degrading, such as a softening, trigger.

Moreover, the present disclosure relates to a method of implanting an electrical or electronic biomedical device according to the present disclosure on a biological surface of a subject, said method comprising a step of handling said electrical or electronic biomedical device through the rigid member.

Further embodiments of the present disclosure are defined by the appended claims.

The above and other objects, features and advantages of the herein presented subject-matter will become more apparent from a study of the following description with reference to the attached figures showing some preferred aspects of said subject-matter. However, the present disclosure is not limited to the embodiments as described in the following and/or depicted in the drawings.

BRIEF DESCRIPTION OF DRAWINGS

In the drawings:

FIG. 1A) bottom view, FIG. 1B) top view;

FIG. 2A) single elongated spine on top surface of the device; FIG. 2B) two elongated channels on top surface of the device; FIG. 2C) three elongated spines on top surface of the device; FIG. 2D) four pillars on the later sides of the device;

In FIGS. 3A and 3B there is depicted a further embodiment of the biomedical device of the present disclosure configured as a brain stem implant; further depicted in FIGS. 3A and 3B is its insertion onto a subject's brain surface by tweezer handling;

FIG. 4A) insertion below the skull in contact with the dura matter following a craniotomy; FIG. 4B) insertion within an intervertebral recess created surgically, to get in contact with the spinal cord.

DETAILED DESCRIPTION

Figure 1A:
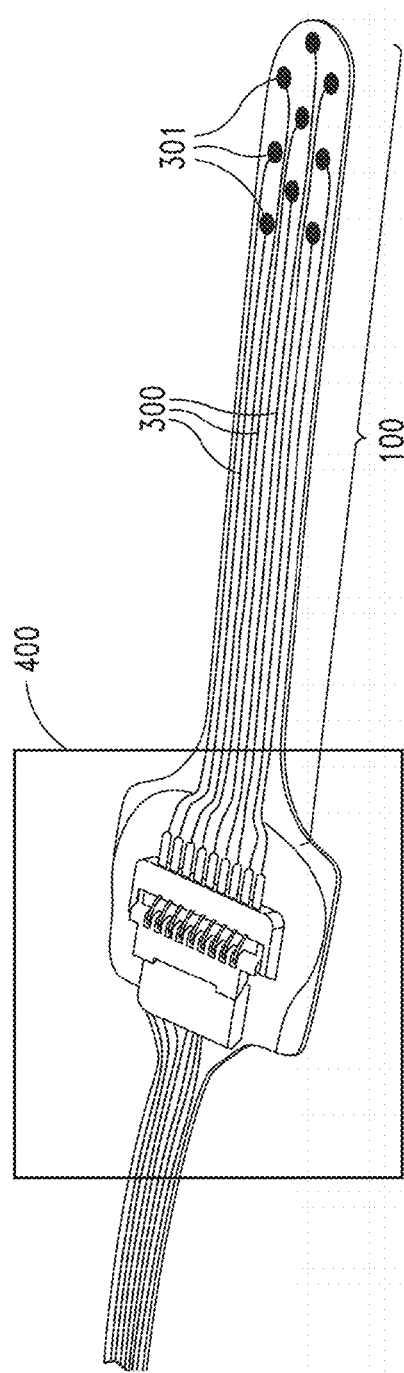
In FIGS. 1A and 1B there is depicted a biomedical device according to an embodiment of the present disclosure.

The present disclosure will be clarified in the following by means of the following description of those embodiments of same which are depicted in the drawings. It is however to be understood that the present disclosure is not limited to the embodiments thereof described in the following and depicted in the drawings. Moreover, it is to be understood that the specific conditions or parameters described and/or shown in the following are not for limiting the subject-matter herein described, and that the terminology used herein is for the purpose of describing particular embodiments of the present disclosure by way of example only.

Unless defined otherwise, technical and scientific terms used herein have the same meaning as commonly understood by one of ordinary skill in the art to which this disclosure belongs. Further, unless otherwise required by the context, singular terms shall include pluralities and plural terms shall include the singular. The methods and techniques of the present disclosure are generally performed according to conventional methods well known in the art and as described in various general and more specific references that are cited and discussed throughout the present specification unless otherwise indicated. Further, for the sake of clarity, the use of the term "about" is herein intended to encompass a variation of +/−10% of a given value.

Non-limiting aspects of the subject-matter of the present disclosure will be described by way of example with reference to the accompanying figures, which are schematic and are not intended to be drawn to scale. For purposes of clarity, not every component is labelled in every figure, nor is every component of each aspect of the disclosure shown where illustration is not necessary to allow those of ordinary skill in the art to understand the disclosure.

The disclosure will be better understood with the use of the following definitions.

As used in the following and in the appended claims, the singular forms "a", "an" and "the" include plural referents unless the context clearly dictates otherwise. Also, the use of "or" means "and/or" unless stated otherwise. Similarly, "comprise", "comprises", "comprising", "include", "includes" and "including" are interchangeable and not intended to be limiting. It is to be further understood that where for the description of various embodiments use is made of the term "comprising", those skilled in the art will understand that in some specific instances, an embodiment can be alternatively described using language "consisting essentially of" or "consisting of."

As used herein, a "polymeric material" is any material comprising polymers, large molecules (also known as macromolecules) composed of many repeated smaller units, or subunits, called monomers, tightly bonded together preferably by covalent bonds. Polymer architecture at the molecular scale can be rather diverse. A linear polymer consists of a long linear chain of monomers. A branched polymer comprises a long backbone chain with several short side-chain branches covalently attached. Cross-linked polymers have monomers of one long or short chain covalently bonded with monomers of another short or long chain. Cross-linking results in a three-dimensional molecular network; the whole polymer is a giant macromolecule. Another useful classification of polymers is based on the chemical type of the monomers: homopolymers consist of monomers of the same type, copolymers have different repeating units. Furthermore, depending on the arrangement of the types of monomers in the polymer chain, there are the following classification: the different repeating units are distributed randomly (random copolymer) or there are alternating sequences of the different monomers (alternating copolymers) in block copolymers long sequences of one monomer type are followed by long sequences of another type; and graft copolymers consist of a chain made from one type of monomer with branches of another type. A sufficiently dense polymer solution can be crosslinked to form a polymer gel, including a hydrogel or a cryogel, which is a soft solid.

Polymer materials may also be formed by blending two or more polymers into physical mixtures. For example, the rather poor impact strength of polystyrene is greatly improved by incorporating small particles of an elastomer. Many properties of polymeric materials depend on the microscopic arrangement of their molecules. Polymers can have an amorphous (disordered) or semicrystalline (partially crystalline, partially ordered) structure. Polymers can be mixed with inorganic particles (usually in the form of continuous fibres, such as glass or particulates such as mica, talc and clay) in order to modify and improve (mainly but not exclusively) their mechanical properties.

A polymer, or monomeric precursors thereof, according to the present disclosure may comprise one or more compounds selected from a non-exhaustive list comprising natural polymeric material (i.e., non-synthetic polymers, polymers that can be found in nature) and/or polymers derived from Extra Cellular Matrix (ECM) as gelatin, elastin, collagen, agar/agarose, chitosan, fibrin, proteoglycans, a polyamino-acid or its derivatives, preferably polylysin or gelatin methyl cellulose, carbomethyl cellulose, polysaccharides and their derivatives, preferably glycosaminoglycanes such as hyaluronic acid, chondroitinsulfate, dermatansulfate, heparansulfate, heparine, keratansulfate or alginate, as well as any derivative thereof, fragment thereof and any combination thereof; thermoset materials such as alkyds, epoxies, phenolics (e.g., Bakelite), polyimides, formaldehyde resins (e.g., urea formaldehyde or melamine formaldehyde), polyester thermosets, unsaturated polyesters, polyurethane, bis-maleimides (BMI), silicone materials such as polydimethylsiloxane (PDMS) and any combination thereof; and other materials such as poly(lactic-co-glycolic acid), lactide and glycolide polymers, caprolactone polymers, hydroxybutyric acid, polyanhydrides, polyesters, polyphosphazenes, polyphosphoesters and poly(glycerol sebacate acrylate), polypropylene, polypropylenoxide or their derivatives, polymethylenoxide or its derivatives, polyethylene or its derivatives such as polyethylene glycole (PEG), polyethylenoxide or their derivatives, polyacrylate or its derivatives such as poly(2-hydroxyethylmethacrylate) (PHEMA), poly(vinyl alcohol) (PVA), poly(lactic acid), poly(methacrylic acid), and copolymers, poly(vinylpyrrolidone) (PVP) and combinations thereof; as well as any combination of the foregoing.

The polymeric materials according to the present disclosure are preferably used to form a soft matrix, so to obtain a soft polymeric material. In the frame of the present disclosure, the expression "soft polymeric material" refers to a polymeric material which is compressible, reversibly compressible, plastically stretchable, reversibly stretchable (elastic), flexible or any combination thereof.

As used herein, the term "gel" refers to a non-fluid colloidal network or polymer network that is expanded throughout its whole volume by a fluid. A gel is a solid three-dimensional network that spans the volume of a liquid medium and ensnares it through surface tension effects. The internal network structure may result from physical bonds (physical gels) or chemical bonds (chemical gels).

As used herein, the term "hydrogel" refers to a gel in which the swelling agent is water. A hydrogel is a macromolecular polymer gel constructed of a network of crosslinked polymer chains. It is synthesized from hydrophilic monomers, sometimes found as a colloidal gel in which water is the dispersion medium. Hydrogels are highly absorbent (they can contain over 90% water) natural or synthetic polymeric networks. As a result of their characteristics, hydrogels develop typical firm yet elastic mechanical properties.

For "mechanically adaptive material" is herein meant a material, such as a polymeric material, which changes its mechanical properties on demand, and in particular upon activation and/or in presence of at least one trigger stimulus. These materials morph upon exposure to a pre-defined stimulus in a highly selective and possibly reversible manner and are attractive for many technologically relevant applications. In the frame of the present disclosure, a trigger stimulus is a degrading trigger, i.e. a stimulus that degrades the rigid member such as for instance a softening trigger, i.e. a stimulus that soften (partially degrades) the rigid member. Degrading or softening triggers according to the disclosure comprise physical stimuli such as temperature, electric field, magnetic field, light, pressure and sound, as well as chemical stimuli such as pH, ionic strength, solvent composition and molecular species.

The expression "conductive track" refers to any film, path, stripe, strand, wire or the like which is electrically conductive in nature. For the sake of clarity, the word "electrode" is herein used to mean the distal part of a conductive track which is in direct contact with a subject's tissue. Conductive tracks according to the present disclosure are used to connect and/or close an electrical circuit, and are thus usually electrical connectors or "interconnects". A conductive track is generally a metallic element that conducts an electric current toward or away from an electric circuit, but can be made of any suitable electrically conductive material, including but not limited to metals such as Au, Pt, Al, Cu and the like, as well as any alloy, oxides and/or combinations thereof; conductive polymeric materials; composite material such as polymeric materials embedding metal particles and/or metal strands or stripes, including insulating materials functionalized with electrically conductive flakes or fibers, for example carbon-filled polymers; liquid metals, including alloys or oxides thereof, such as gallium; electrically conductive inks; as well as any suitable combination thereof.

The expressions "film" or "thin film" relate to the thin form factor of an element of the biomedical device of the disclosure such as a support substrate and/or a conductive track. Generally speaking, a "film" or "thin film" as used herein relates to a layer of a material having a thickness much smaller than the other dimensions, e.g. at least one fifth compared to the other dimensions. Typically, a film is a solid layer having an upper surface and a bottom surface, with any suitable shape, and a thickness generally in the order of nanometers, micrometers or even millimetres, depending on the needs and circumstances, e.g. the manufacturing steps used to produce it. In some embodiments, films according to the disclosure have a thickness comprised between 0.1 µm and 5 mm, such as between 5 µm and 5 mm, between 5 µm and 1 mm, between 10 µm and 1 mm, between 5 µm and 500 µm, between 50 µm and 500 µm between, between 50 µm and 150 µm, 100 µm and 500 µm or between 200 µm and 500 µm.

As used herein, a "biodegradable material" refers to a material manufactured of polymer, copolymer or polymer composition, the degradation and/or absorbing of which material takes place by means of metabolic, chemical and/or physical reactions. The degradant component may increase the rate of degradation of the polymer by a process that involves one or more of, for example, photodegradation, biodegradation, or chemical degradation. In addition, mechanical forces such as erosion may further help degrade the polymer. Photodegradation means a process of degradation that is initiated by exposure of the polymer to natural or artificial light. Biodegradation means a process of degradation that occurs as a result of the action of enzymes, derived from the metabolic processes of a subject, on the polymer. Chemical degradation means a process of degradation wherein chemical bonds in the polymer are broken as a result of one or more chemical reactions such as, for example, hydrolysis, thermal cleavage, or oxidation. Chemical degradation is thus more encompassing than photodegradation, since the reactions are not limited to those initiated by exposure to light. It is possible that a given mechanism of degradation may be classified as more than one of the above-described processes. Non-limiting, exemplary degradation mechanisms comprise UV light, liquid uptake, temperature change, application of a magnetic or electric field, pH change, pressure change and/or ionic strength change.

The term "degradation" encompasses either a full degradation, in which the material is totally degraded so that it disappears, or a partial degradation which alters the chemical and/or physical properties of the degraded material, such as the Young's modulus or the density of the degraded material, while keeping the material in place. In this context, for the sake of clarity, in the frame of the present disclosure a "partial degradation" can also be called "softening". Of note, a partial degradation or softening can be, in some embodiments, reversible, such as for instance in the case of removal or reversal of the degrading conditions. Further, a degradation process can be complete such that the entirety of the material is affected by the degradation process, or uncomplete, such that only a fraction of the material is degraded, such as about the 50, 60, 70, 80, 90, 95 or 99% of the volume and/or the weight of the material.

As used herein, a "fast-degradable material" refers to a degradable material that can be degraded by one or more of the above-listed degradation mechanisms, completely or partially, in a time lapse comprised between 1 minute and 1 week, such as for instance 2, 3, 4, 5, 6 or 7 days, as well as in a time lapse comprised between 10 minutes to 24 hours, such as for instance between 15 and 60 minutes, or between 30 and 120 minutes.

As used herein, "treatment" and "treating" and the like generally mean obtaining a desired physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it for example based on familial history, overweight status or age; (b) inhibiting the disease, i.e., arresting its development; or relieving the disease, i.e., causing regression of the disease and/or its symptoms or conditions such as improvement or remediation of damage.

The term "subject" as used herein refers to mammals. For example, mammals contemplated by the present disclosure include human, primates, domesticated animals such as cattle, sheep, pigs, horses, laboratory rodents and the like.

Figure 1B:
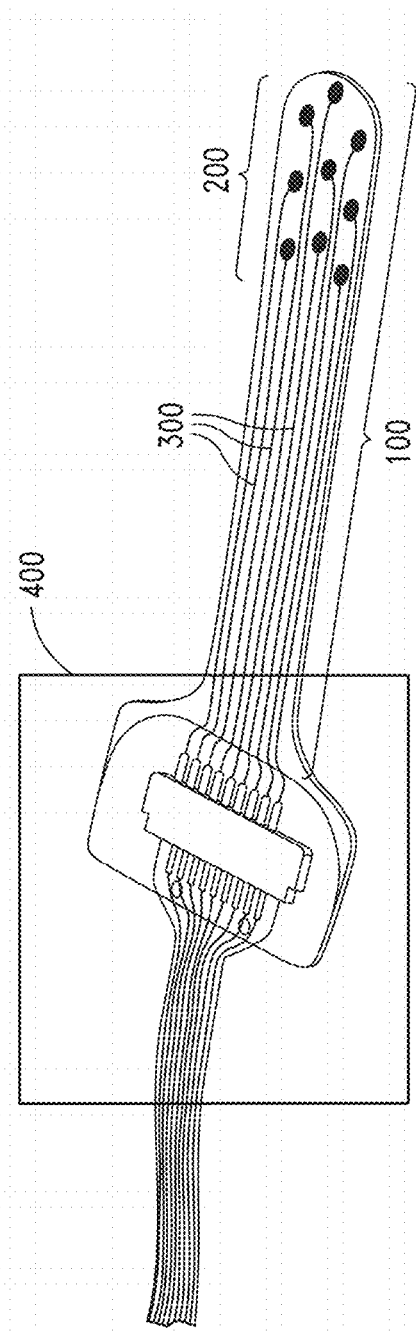
Figure 2B:
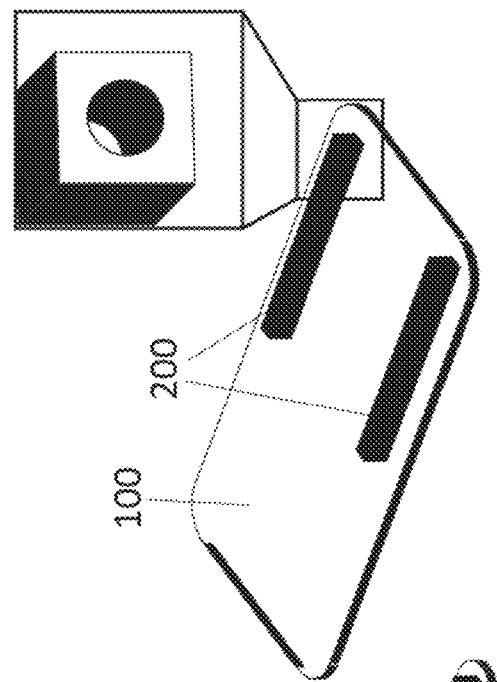
In FIGS. 2A, 2B, 2C, 2D there are depicted the biomedical devices according to embodiments of the present disclosure differing as to the positioning of a rigid member.
Figure 2D:
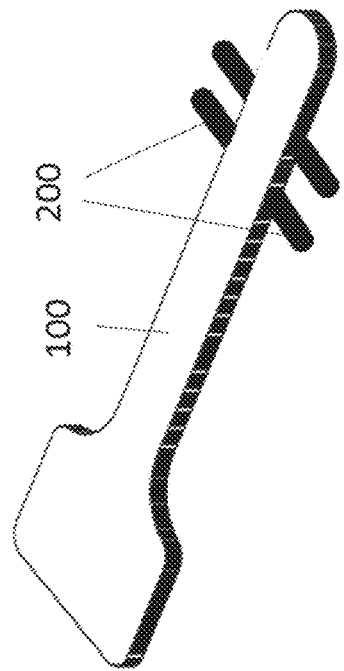
Figure 2A:
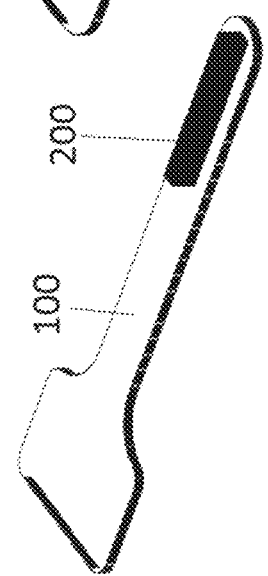
Figure 2C:
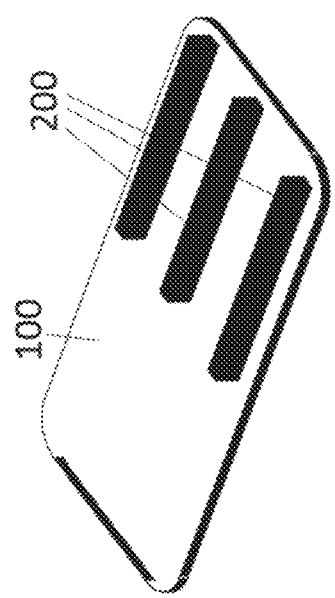

With reference to FIGS. 1A and 1B, a bottom view (FIG. 1A) and a top view (FIG. 1B) of one embodiment of the biomedical device according to the present disclosure are depicted. The device comprises a flat and soft substrate 100, comprising electrically conductive tracks 300, the substrate 100 being configured to interface a biological surface; further depicted is a rigid member 200 located on a portion of said flat and soft substrate 100, said member 200 being substantially composed of a mechanically adaptive material being fully or partially degradable upon a degrading, such as a softening, trigger. Substrate 100 can be provided in a multiplicity of shapes, such as a rectangular, elongated, circular, squared, "dogbone" like etc., the substrate 100 defining, as in the depicted embodiment, an upper surface and a bottom surface. The flat appearance of the substrate 100 is particularly suitable for interfacing the biomedical device with biological surfaces, as will be detailed in the following.

As to the materials of the substrate 100, according to preferred embodiments the substrate 100 is substantially made of a soft polymeric material, or combinations of many soft polymeric materials, particularly biocompatible ones. Preferred soft materials are elastomeric materials, thermoplastic elastomers (a class of copolymers or a physical mix of polymers, usually a plastic and a rubber, which consist of materials with both thermoplastic and elastomeric properties), foams, gels or hydrogels. As a way of example, the substrate 100 can be substantially composed of one or more polymer selected from a non-exhaustive list comprising thermoset materials such as alkyds, epoxies, phenolics (e.g., Bakelite), polyimides, formaldehyde resins (e.g., urea formaldehyde or melamine formaldehyde), polyester thermosets, unsaturated polyesters, polyurethane, bis-maleimides (BMI), silicone materials such as polydimethylsiloxane (PDMS) and any combination thereof; and other materials such as poly(lactic-co-glycolic acid), lactide and glycolide polymers, caprolactone polymers, hydroxybutyric acid, polyanhydrides, polyesters, polyphosphazenes, polyphosphoesters and poly(glycerol sebacate acrylate), polypropylene, polypropylenoxide or their derivatives, polymethylenoxide or its derivatives, polyethylene or its derivatives such as polyethylene glycole (PEG), polyethylenoxide or their derivatives, polyacrylate or its derivatives, poly(vinyl alcohol) (PVA), poly(lactic acid), poly(methacrylic acid), and copolymers, poly(vinylpyrrolidone) (PVP) and combinations thereof; as well as any combination of the foregoing.

According to an embodiment, the substrate 100 is an elastomeric substrate, for instance a PDMS substrate. The substrate 100 can be implemented as a thin film substrate, having a thickness comprised between about 1 µm and about 5 mm, such as between about 5 µm and about 5 mm, between about 5 µm and about 1 mm, between about 10 µm and about 1 mm, between about 5 µm and about 500 µm, between about 50 µm and about 500 µm, between about 50 µm and about 150 µm, between about 100 µm and about 500 µm or between about 200 µm and about 500 µm.

The substrate 100 may be reversibly stretchable (elastic). In particular, the substrate 100 can withstand an elongation or multidirectional strain, upon a single or multiple cycles, comprised between 1 and 500%, preferably at least 5%, such as about 50%, about 100% or about 200%, of its size at rest without cracking or loss of its mechanical properties. Further, the substrate 100 may have a Young's modulus comprised between about 1 kPa and 10 GPa, such as for instance between about 100 kPa to about 5 GPa, between about 100 kPa to about 1 GPa, between about 5 MPa to about 1 GPa, between about 1 GPa to about 5 GPa, between about 100 kPa to about 100 MPa, between about 100 kPa to about 5 MPa, between about 10 kPa to about 300 kPa or between about 10 kPa to about 10 MPa, which are suitable ranges of values matching the Young's modulus of many biological tissues and surface to avoid mechanical mismatches between said tissues and a biomedical device, and/or for mimicking physical and/or mechanical properties of bodily tissues. In the frame of the present disclosure, "physical and/or mechanical properties" means, by way of examples, stress-strain behaviour, elastic modulus, fracture strain, conformability to curvilinear surfaces, thickness, area and shape which have to be as similar as possible to those to be found in tissues of a subject's body.

On the flat and soft substrate 100 of the biomedical device according to the embodiment there are disposed electrically conductive tracks 300. Typically, in one set of embodiments, said conductive tracks 300 allow electrical interconnection to be established between a subject's tissue and further electrical and/or electronic devices such as for instance electrical stimulators, PCBs, microchips, connectors, wires and the like. Each of conductive tracks 300 (or at least one of them) can preferably comprise a distal, end electrode portion 301 configured to directly interface a bodily tissue. The conductive tracks 300 and/or the respective end electrodes 301 can be made of any suitable electrical conductive material, including but not limited to metals such as Au, Pt, Al, Cu, Pt—Ir, Ir, and the like, as well as any alloy thereof, oxide thereof and combinations thereof, composite metal-polymer materials, such as Pt-PDMS composites or Pt—Ir-PDMS composites or Ir-PDMS composites and so forth, as well as conductive polymers such as PEDOT:PSS. In a preferred embodiment, the electrodes are made of non-toxic and biocompatible materials. Conductive tracks 300 and/or end electrodes 301 can be placed on or (at least partially) embedded within the substrate 100 with any suitable means such as for instance photolithography, electron beam evaporation, thermal evaporation, sputter deposition, chemical vapour deposition (CVD), electro-plating, molecular beam epitaxy (MBE) or any other conventional means known in the art. Conductive tracks 300 are preferably encapsulated later on to avoid short circuits and failure thereof, i.e. passivated whilst leaving the electrodes 301 exposed through connecting vias.

According to a plurality of embodiments according to the present disclosure, at least one of the conductive tracks 300 is a compliant interconnect. A "compliant interconnect" is any structure or element able to deliver an electric current, and adapted to change its shape according to the shape change of the support it is provided on and/or embedded (at least partially in) and/or adheres to or the like, without substantially compromising (changing) its mechanical and/or electrical performances. The term "compliant" is intended to include any conformable structure which is compressible, reversibly compressible, elastic, flexible, stretchable or any combination thereof. Examples of compliant electrodes known in the art include metal thin-films (including patterned electrodes, out-of-plane buckled electrodes, and corrugated membranes), metal-polymer nano-composites, carbon powder, carbon grease, conductive rubbers or conductive paints, a review of which is provided in Rosset and Shea (Applied Physics A, February 2013, Volume 110, Issue 2, 281-307. As it will be apparent to those skilled in the art, built-in multilayers or stacks of several layers of any of the above polymeric, composite, metallic and/or oxide materials, as well as combinations thereof, are encompassed in the definition of compliant interconnect. In some embodiments of the present disclosure, stretchable interconnects as the ones described in International Patent Applications WO 2004/095536, WO 2016/110564 and/or WO 2018/100005A1 can be used.

According to a plurality of embodiments, the biomedical device of the present disclosure comprises one or more arrays of elastically stretchable microelectrodes. As used herein, for the sake of clarity and conciseness, a "stretchable microelectrode array" refers to the ensemble of a plurality of interconnects 300 and respective distal electrodes 301 having the ability to withstand mechanical deformations such as flexing, stretching, torsion or the like, without electrical failure or loss of their electrical features. Stretchable arrays (for instance stretchable gold and/or Cr/Au microelectrode arrays, MEAs) are becoming more and more popular and find convenient applications in the field of wearable electrodes, and/or implantable neuroprosthetic interface applications, and/or as electrode arrays for cell culture and tissue slice culture, and/or even for sensing robotic skins or the like. Accordingly, microelectrode arrays are particularly suitable to be used as a neural interface with the spinal cord, brain or peripheral nerves or soft biological tissue, for instance for the purpose of stimulating and/or recording neurological or cardiac activity, as well as for monitoring hippocampal electrical activity after traumatic brain injury or bladder afferent activity, or even for stimulating electrical potential of excitable cells or the like.

It has in fact been verified that the impedance of microelectrode arrays stays low and stable during the deformation and even after repeated torsions, and therefore facilitate the recording of small amplitude biological signals and ensure efficient functional electrical stimulation, as well as no or little degradation of the implant even after several months from implantation.

The electrical connection between electrodes interconnects 300 and one or more electrical and/or electronic device 400 can be done in any suitable way. With reference for instance to FIGS. 1A and 1B, in one embodiment of the present disclosure some connection wires (not depicted) extends from the interconnects 300 to the one or more electrical and/or electronic device 400, where e.g. an electrical pad electrically couples said wires to said device 400.

One of the key features of the biomedical device of the present disclosure relates to the presence of a rigid member 200 located on a portion of said flat and soft substrate 100, said member 200 being substantially composed of a mechanically adaptive material becoming soft upon a degrading, such as a softening, trigger, as exemplary depicted in FIGS. 2A-2D. The device of the present disclosure features a rigidifying member that is grafted on localized portions of said device. When the member 200 is in its rigid form, it temporary rigidifies a portion of the biomedical device, which allows an easy handling and surgical insertion by a clinician. The increase of the apparent stiffness due to the member 200 is however reversible: once the biomedical device is correctly positioned on the targeted biological surface, the mechanically adaptive material substantially composing the rigidifying member 200 fully recovers its intended conformability by providing a degrading, such as a softening, trigger, without any impact on the initial mechanical properties of the entire device, thus allowing the entire device to recover its initial softness. The advantage of the invented configuration is the provision of combining the easy handling of the soft biomedical device by an operator (e.g. a surgeon) with its easy insertion in cavities or recesses, thus facilitating a minimally invasive approach. This is obtained in particular by the positioning and the very nature of the rigid member 200, acting as an anchoring point for surgical tools such as tweezers.

The location of the rigidifying member 200 can be precisely chosen in advance, thus permitting an extreme tailoring on demand of the handling of the biomedical devices, depending on the needs and circumstances. Moreover, the kind of polymer(s) substantially composing the rigidifying member 200 can be chosen on demand in advance so as to decide the needed time of degradation thereof.

Compared to prior art approaches, the present solution enables insertion of soft elastomer-based biomedical devices in various locations of a subject's body, and particularly on those biological surfaces which are barely accessible, with a minimally invasive approach. In fact, contrary to previous attempts using a softening backing to rigidify the entirety of a soft and stretchable device, the design of the present disclosure permits to keep at all times the softness of said device, which would be otherwise brittle and fragile than pure elastomer and therefore more prone to breakage, failure or partial crack during manipulation, thus hugely facilitating the handling and operations of a surgeon even with the use of surgical tools.

Preferably, the rigid member 200 is substantially made of a solidified paste, gel or hydrogel. In one preferred embodiment, the rigid member 200 of the present disclosure is substantially made of a hydrogel, in particular a dry hydrogel in its rigid form.

Several physical properties of the hydrogels are dependent upon concentration. Increase in hydrogel concentration may change its pore radius, morphology, or its permeability to different molecular weight proteins. One skilled in the art will appreciate that the volume or dimensions (length, width, and thickness) of a hydrogel-made rigid member can be selected based on instant needs, such as for instance the region or environment into which the hydrogel is to be located.

The mechanical properties of the material composing the rigid member 200 can be tailored according to the needs by changing the physical or chemical properties thereof (molecular chain length, crosslinking rate, water content, and so forth). In this context, in order to optimize the mechanical properties of the material of the rigid member and, in some aspects, its resorption/biodegradation rate, in preferred embodiments an average molecular weight for the macromolecules substantially composing the polymeric material of the rigid member 200 is contemplated so as to be comprised between about 1,000 and about 5,000,000 g/mol, along with a polymer density of at least 0.1 g/cm$^3$. A polymer density comprised between about 0.5 and about 2 g/cm$^3$ is considered to be a suitable density for the rigid member material according to the disclosure. In some embodiments, the polymeric rigid member material can be either physically or chemically crosslinked or minimally crosslinked in order to e.g. favour the fast biodegradation thereof. In the case of chemical crosslinking, specific agents and their amount can be chosen at the operator's discretion, and a skilled in the art would easily envisage such parameters based on common practice.

As to the degradation/resorption rate of the rigid member 200, particularly upon in vivo application/implant in a host, same is mainly dependent on physical-chemical properties of the polymeric material of which it is composed of, as well as further factors such as crosslinking of the polymers, the polymer concentration, the site of implant into a host and the like. Generally speaking, the rigid member 200 is substantially composed of a mechanically adaptive material that is fully or partially degradable or biodegradable when in contact for a suitable amount of time with a degrading, such as a softening, trigger. In both cases, a degrading trigger is used to drive the degradation so as to let completely disappear the member 200, or softening the member 200 to match the mechanical and/or physical properties of the surrounding bodily tissue. Accordingly, the rigid member 200 is substantially made of a material which is subject to a partial or full degradation brought about by one or more degrading, such as a softening, triggers selected from a non-exhaustive list of triggers comprising UV light, liquid uptake, temperature change, pH change and/or ionic strength change. In this context, the rigid member 200 in its soft form (i.e. upon partial or full degradation) has a Young's modulus comprised between about 0 (in case of a full degradation) and 100 MPa, as well as any values in between. As a way of example, a polymeric material substantially composing the rigid member 200 can be softened by the application of a UV light upon implant in a subject, the uptake of liquids such as water or cerebrospinal fluid (CSF), as well as the raise of temperature when put into contact with a biological surface, from e.g. about 25° C. to about 37° C. In some embodiments, moreover, the rigid member 200 is substantially made of a fast-degradable material, or configured to be fast degraded by, for instance, engineering its porosity, its 3D structure and the like.

To this aim, the inventors have identified some preferred, but not limiting, polymeric materials for constituting the rigid member 200, said materials comprising acrylate-based polymers such as poly(2-hydroxyethyl methacrylate) [PHEMA], acrylamide-based polymers, polymers of acrylic acid and/or salts thereof including sodium and sulfopropyl acrylates, polyvinylpyrrolidone-based polymers, poly(vinyl alcohol) [PVA], poly(ethylene glycol), gelatin-based polymers, dextran-based polymers, poly(lactic acid), cellulose-based polymers, chitosan-based polymers, silk-based polymers, hyaluronic acid-based hydrogel, cyclodextrin-based polymers, alginate-based polymers as well as combinations of any of the foregoing. Advantageously, such polymers can be used to produce fast-(bio)degradable materials, which can be furthermore formulated as hydrogels that can be dried to become rigid.

As anticipated, the rigid member 200 is located, in the frame of the present disclosure, on (a) limited portion(s) of the support 100, and preferably on no more than 80% of the total surface of one or both of the lower and upper surfaces of the support 100, more preferably no more than 50% of the total surface, no more than 40% of the total surface, no more than 30% of the total surface, no more than 20% of the total surface, no more than 10% of the total surface or no more than 5% of the total surface of the support 100. In particular, in some embodiments the rigid member 200 is located on a surface of said flat and soft substrate 100, particularly on the surface opposite to the surface where electrodes 301 are exposed, and can have many different shapes such as a U-shape, a dome, an elongated spine, a pillar or a channel. Moreover, in some embodiments as those depicted in FIGS. 2A-2D, more than one rigid member 200 can be provided, depending on the needs or circumstances, so that a plurality (or "array") of pillars, spines etc. are present. The various configurations depend mainly on the type of surgery to be performed, the tools used to perform said surgery, the location of implant and so forth. For instance, if a tweezer is used to insert a biomedical device according to the disclosure into a brain cavity, a spine configuration can be useful to grasp the device comfortably, whereas two channel-shaped rigid members 200 are advantageous in case the device needs to be stretched or compressed by manipulating the tweezer, the tips thereof having been previously inserted into the channels' bores (see FIG. 2B). In some additional or alternative embodiments, moreover, the rigid member 200 can be located on the flat substrate 100, so as to be parallel to the plane the substrate 100 lies on, as depicted for instance in FIG. 2D.

The electrical or electronic biomedical device of the disclosure can be configured as a fixed or removable neural implant, heart implant, kidney implant, pancreatic implant, bladder implant, retina implant, gut implant or vascular implant. Within the meaning of the present disclosure, a "fixed implant" defines a biomedical device having the ability to conform to established and/or customised surgical procedures and to reside in vivo without producing adverse biological reactions over extended periods of time. Still within the meaning of the present disclosure, a "removable implant" defines a biomedical device having the ability to conform to established and/or customised surgical procedures and to reside in vivo for a limited amount of time, such as for instance the time of a surgical operation.

As anticipated, the present disclosure relates as well to a method of manufacturing an electrical or electronic biomedical device, said biomedical device comprising a flat and soft substrate 100, said method comprising a step of placing a rigid member 200 on a portion of said flat and soft substrate 100, said member 200 being substantially composed of a mechanically adaptive material being fully or partially degradable upon a degrading, such as a softening, trigger.

In a non-limiting, implemented and exemplary embodiment of the present disclosure, the method comprises a first step in which a rigid member 200 is prepared by free radical polymerization of 60 wt % HEMA monomer solubilized in ethanol with 0.2 mol % of ethyleneglycol dimethacrylate crosslinker to obtain a poly(2-hydroxyethyl methacrylate) (PHEMA) hydrogel rigid member. The solution is prepolymerized by photoinitiation at 365 nm in order to increase its viscosity for patterning purposes; the resulting solution is called "PreGel-Glue". At this point, the PreGel-Glue can be either patterned on PET substrate by casting to prepare micrometric dry hydrogel films or poured in mold to prepare millimetric backings. The PreGel-Glue polymerization is completed by photopolymerization at 365 nm for 10 minutes. The casting process leads to thicknesses of dry hydrogels from about 50 to about 200 µm. The polymerized films can then be cut via laser or blade machining to match the shape of the biomedical device that needs to be equipped with the rigid member. The molding process leads to thicknesses of dry hydrogels from about 200 µm to about 3 mm. The rigid member can be shaped via razor blade cutting.

In a second step, the material constituting the substrate 100 is chemically modified by grafting of trimethoxysilyl propylmethacrylate (TMSPMA) on its top surface. The material is first plasma etched for 30 seconds ($O_2$: 0.5 mbar, Power: 20 W). Then a vapor phase silanization of the activated material is performed, leading to the grafting on the material of methacrylate groups.

To glue the hydrogel member to the reactive surface of the substrate 100, some drops of PreGel-Glue are deposited on a surface (lower and/or upper) of the substrate 100 and the rigid member hydrogel is located on it, ensuring a full wet contact between the rigid member 200 and the soft substrate 100. Finally, the polymerization of the PreGel-Glue is completed via photopolymerization.

The dry hydrogel rigid member (200) gives to the device a sufficient local rigidity allowing it to be inserted in small cavities. Once the device is well positioned in the cavity, the initially dry hydrogel (Young modulus about 2 GPa) starts to uptake water from the wet body environment. When the hydrogel is in contact with liquid (such as water, or cerebrospinal fluid), the liquid diffuses in the hydrogel and softens it by 4 orders of magnitude. The hydrogel swelling leads to the mechanical softening of the previously rigid member 200 (Young modulus about 200 kPa) and enables the full recovery of the device conformability: the hydrogel then becomes almost mechanically invisible, and the device recovers its initial softness. It is also important to notice that the hydrogel has a limited swelling (~30-50 vol %), avoiding side-effects due to compression of the surrounding tissues.

The present disclosure further relates to a method of implanting an electrical or electronic biomedical device according to the present disclosure on a biological surface of a subject, said method comprising a step of handling said electrical or electronic biomedical device through the rigid member 200. Preferably, said handling is performed through a surgical instrument such as a tweezer, a cannula, a dilator, a forcep, a needle holder, a clamp and the like. In the frame of e.g. a surgical implant of a biomedical device of the disclosure, the method can further comprise a step of providing a degrading, such as a softening, trigger to the rigid member 200 selected from a list comprising UV light, liquid uptake, temperature change, pH change and/or ionic strength change.

As it will be apparent to a person skilled in the art, the method can further comprise a step of introducing said electrical or electronic biomedical device into a cavity or recess of a subject. For "cavity" or "recess" is herein meant any natural or artificially (e.g. surgically) created path in a subject's body that allows for reaching a biological surface inside said subject's body in a minimally invasive manner. Accordingly, the definition is meant to include bodily cavities such as the cranial cavity, the spinal cavity, the ventral body cavity, the thoracic cavity, the abdominopelvic cavity, the abdominal cavity or the pelvic cavity, as well as a brain sulcus, a lumen, a sinus, a ventricle and the like. Accordingly, the method foresees implanting an electrical or electronic biomedical device according to the present disclosure on a biological surface located on a portion of the brain, the heart, the gut, the pancreas, the bladder, a blood vessel, a kidney and/or an eye of said subject. As a way of example, the biomedical device of the disclosure has been used in the context of an auditory brainstem implant (ABI, FIGS. 3A and 3B). The anatomical target of the ABI is situated in a recess, between the cerebellum and the brainstem. It is therefore necessary to put the implant in that recess. This is almost impossible if the implant is too soft and floppy. The inventors were able to demonstrate that adding a rigid member on the implant allows a much easier insertion, and at the same time allows the implant to recover its softness and conformability once implanted.

Figure 4A:
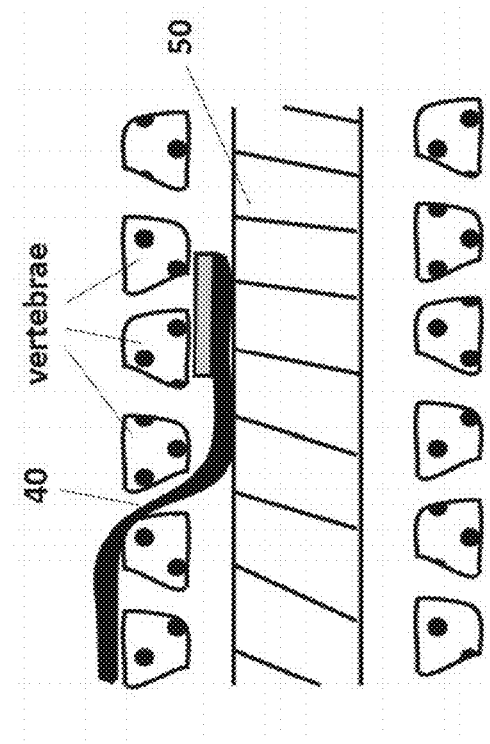
In FIGS. 4A and 4B there are depicted the use and insertion of the biomedical device of the present disclosure.
Figure 4B:
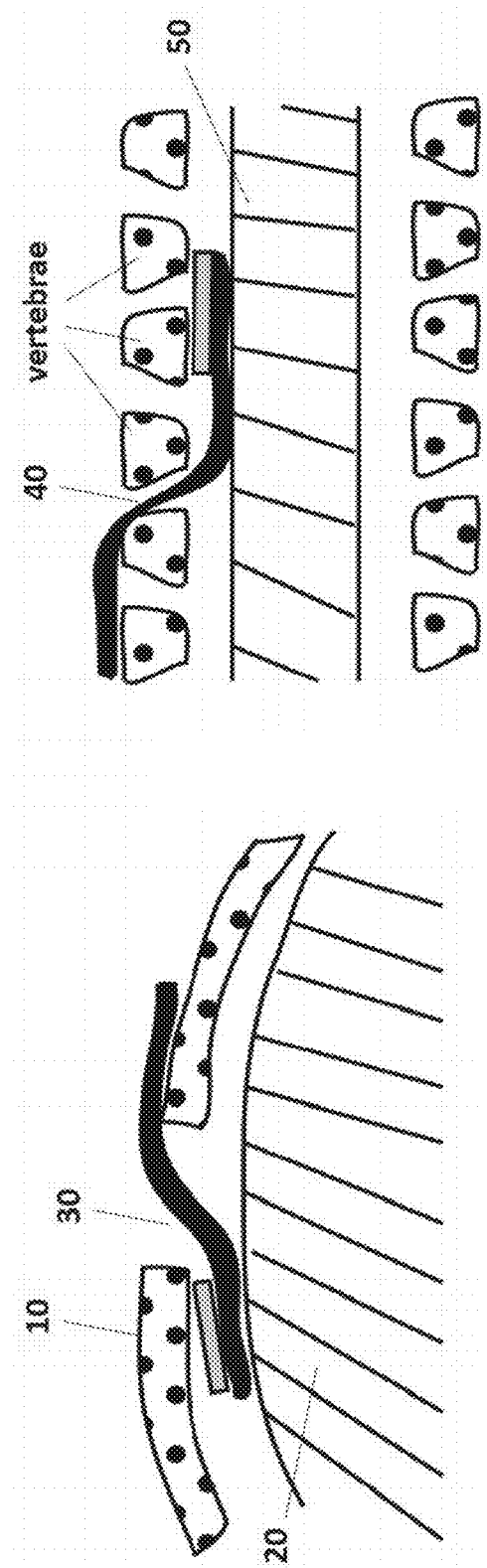

In additional examples as depicted in FIGS. 4A and 4B, the biomedical device can be inserted below the skull 10 in contact with the dura matter 20 following a craniotomy 30 (FIG. 4A), or within an intervertebral recess 40 created surgically, to get in contact with the spinal cord 50 (FIG. 4B).

In an additional or alternative set of embodiments, the method can further comprise a step of introducing said electrical or electronic biomedical device into a cavity or recess of a surgical tool. As a way of example, the biomedical device of the disclosure can be easily introduced into a catheter by taking advantage of the rigid member 200 and let it slide therein while keeping a bent, twisted or otherwise deformed configuration up to the target biological surface inside a subject's body. This is particularly advantageous in certain minimally invasive surgical operations in the interventional radiology field such as for brain or heart surgeries.

The device and methods according to the present disclosure can be used and respectively carried out in a variety of situations for treating one or more pathological conditions. A non-limiting, exemplary list of uses of the biomedical device of the present disclosure comprises retinal, subretinal, and suprachoroidal implants or prosthesis for the treatment of degenerative retinal diseases such as retinitis pigmentosa or age-related macular degeneration (AMD); phrenic nerve stimulators and diaphragm pacemakers to restore breathing function in patients with breathing disorders such as central hypoventilation syndrome (CCHS), central sleep apnea, and diaphragm paralysis; cochlear implants or auditory brainstem implants for the treatment of partial or profound deafness resulting from inner ear damage; stimulation of the brainstem for the treatment of tinnitus; stimulation of the brain for recovery in stroke patients or to treat migraines; electrocorticography (ECoG) to record electrical activity from the cerebral cortex; pacemakers and implantable cardioverter defibrillators; electrical recording for epicardial and endocardial mapping; bladder implants for the treatment of bladder disorders such as detrusor hyperreflexia, detrusor areflexia, overactive bladder syndrome, and urine retention; electrical stimulation of the sphincter for constipation; electrical stimulators for the therapy of pain relief and management thereof, for Parkinson's disease, dystonia or epilepsy; peripheral nerve stimulators for e.g. stimulation of the common peroneal nerve to provide dorsiflexion of the foot and restore muscle movements; lower esophagus stimulators for preventing or treating gastroesophageal reflux; vagal blocking devices for the treatment of obesity by suppressing the sensation of hunger; neuronal interfaces for treating spinal cord injury, strokes or degenerative disorders such as amyotrophic lateral sclerosis cerebral palsy, muscular dystrophy and chronic neuropathic pain, and the like.

While the disclosure has been disclosed with reference to the preferred embodiments thereof as depicted in the drawings, numerous modifications, alterations, and changes to the described embodiments, and equivalents thereof, are possible without departing from the sphere and scope of the disclosure. Accordingly, it is intended that the disclosure is not limited to the described embodiments.

The invention claimed is:

1. An electrical or electronic biomedical device comprising:
   a soft substrate composed of a polymeric material selected from elastomeric materials, thermoplastic elastomers, foams, gels, hydrogels or combinations thereof, the soft substrate having a first surface and an opposed surface;
   wherein said first surface and opposed surface are outer surfaces of the soft substrate;
   at least one electrically conductive track fixed to said substrate and configured to interface with a biological surface, the at least one electrically conductive track extending along a first portion of said substrate and within said first portion, the first portion arranged between a proximal end and a distal end of the substrate; and
   a rigid member composed of a mechanically adaptive material configured to be softened upon a softening trigger or fully degradable upon a degrading trigger, the rigid member extending only along a limited portion of the substrate and on said limited portion, the limited portion being within said first portion of the substrate,
   wherein a remaining portion of said first portion, outside the limited portion, is free from the rigid member,
   wherein the at least one electrically conductive track extends along and within said remaining portion which is free from the rigid member,
   wherein the rigid member is located on at least one of the first surface and the opposed surface;
   wherein the rigid member is located on no more than 80% of the total surface of one or both of said first surface and opposite surface of the soft substrate,
   wherein the rigid member is configured to be softened by at least one of UV light, liquid uptake, temperature change, pH change and ionic strength change.

2. The electrical or electronic biomedical device of claim 1, wherein said substrate is configured as a flat thin film surface and wherein said rigid member is shaped as a U-shape member, a dome, an elongated spine, a pillar or a channel.

3. The electrical or electronic biomedical device of claim 1, wherein said rigid member is made of a solidified paste, solidified gel, or dry hydrogel.

4. The electrical or electronic biomedical device of claim 3, wherein said hydrogel has a density comprised between about 0.1 and about 2 g/cm$^3$.

5. The electrical or electronic biomedical device of claim 1, wherein said rigid member is composed of a compound selected from a list consisting of acrylate-based compounds including poly(2-hydroxyethyl methacrylate) [PHEMA], acrylamide-based compounds, acrylic acid and/or salts thereof including sodium and sulfopropyl acrylates, polyvinylpyrrolidone-based compounds, poly(vinyl alcohol) [PVA], poly(ethylene glycol), gelatin, dextran, poly(lactic acid), cellulose, chitosan, silk, hyaluronic acid-based hydrogel, cyclodextrin, alginate and combinations of any of the foregoing.

6. The electrical or electronic biomedical device of claim 1, wherein the electrical or electronic biomedical device is configured as a fixed or removable neural implant, a fixed or removable heart implant, a fixed or removable kidney implant, a fixed or removable pancreatic implant, a fixed or removable bladder implant, a fixed or removable retina implant, a fixed or removable gut implant or a fixed or removable vascular implant.

7. The electrical or electronic biomedical device of claim 1, wherein said at least one conductive track is passivated while leaving an end electrode portion exposed.

8. The electrical or electronic biomedical device of claim 1, wherein said rigid member has a Young's modulus decreasing below 100 MPa when exposed to one of UV light, liquid uptake, temperature change, pH change and ionic strength change.

9. The electrical or electronic biomedical device of claim 1, wherein said first surface and opposed surface are flat.

10. The electrical or electronic biomedical device of claim 9, wherein a thickness of the soft substrate is uniform.

11. The electrical or electronic biomedical device of claim 1, the soft substrate is formed by said polymeric material and no space is formed between said first surface and opposed surface.

12. The electrical or electronic biomedical device of claim 1, wherein the at least one electrically conductive track does not extend within the limited portion wherein the rigid member is located.

* * * * *